United States Patent [19]

Meer

[11] Patent Number: 4,778,448

[45] **Date of Patent: * Oct. 18, 1988**

[54] NASO-ENTERAL TUBE HARNESS APPARATUS AND METHOD

[76] Inventor: Jeffrey A. Meer, 7380 St. Auburn, Birmingham, Mich. 48010

[*] Notice: The portion of the term of this patent subsequent to Jan. 6, 2004 has been disclaimed.

[21] Appl. No.: 884,081

[22] Filed: Jul. 10, 1986

Related U.S. Application Data

[63] Continuation-in-part of Ser. No. 774,485, Sep. 10, 1985, Pat. No. 4,634,425.

[51] Int. Cl.[4] .............................................. A61M 25/00

[52] U.S. Cl. ....................................... 604/54; 604/174; 604/280; 128/207.18; 128/DIG. 26

[58] Field of Search ..................... 604/54, 77, 94, 174, 604/270, 271, 280; 128/207.18, DIG. 26

[56] References Cited

U.S. PATENT DOCUMENTS 3,161,199 12/1964 Sands ................................ 128/D26
4,050,667 9/1977 Kossett ................................ 604/281
4,133,315 1/1979 Berman et al. ......................... 604/96
4,634,425 1/1987 Meer .................................... 604/54

OTHER PUBLICATIONS

Barrocas et al., "The Bridle: Increasing the Use of Nasoenteric Feedings", *Nutritional Support Services* vol. 2, No. 8, Aug. 1982.
McGuirt, Strout, "Securing of Intermediate Duration Feeding Tubes," *The Laryngoscope,* vol. 90, pp. 2046–2048 (1980).

*Primary Examiner*—Stephen C. Pellegrino
*Assistant Examiner*—Ralph Lewis
*Attorney, Agent, or Firm*—Robert M. Isackson

[57] ABSTRACT

A harness for a tube for use in patient health care, particularly for naso-enteral feeding. The harness is a thin elongated length of material, preferably cylindrical or tubular, secured to a nasal tube for a distance along the length of the tube and inserted into the patient with the tube. The harness then may be secured about the patient's nasal septum so that the connection between the harness and the tube along the distance is within the patient's nostril.

13 Claims, 4 Drawing Sheets

FIG. 1
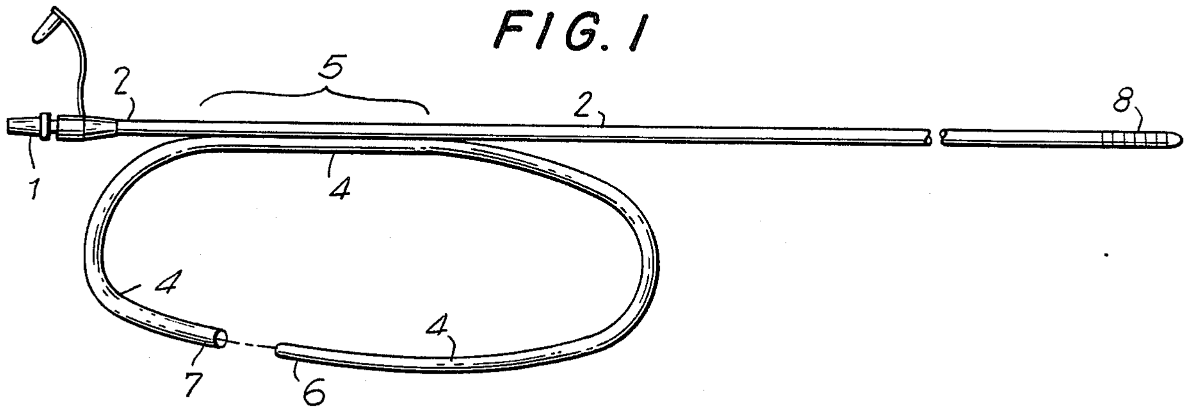
FIG. 2A
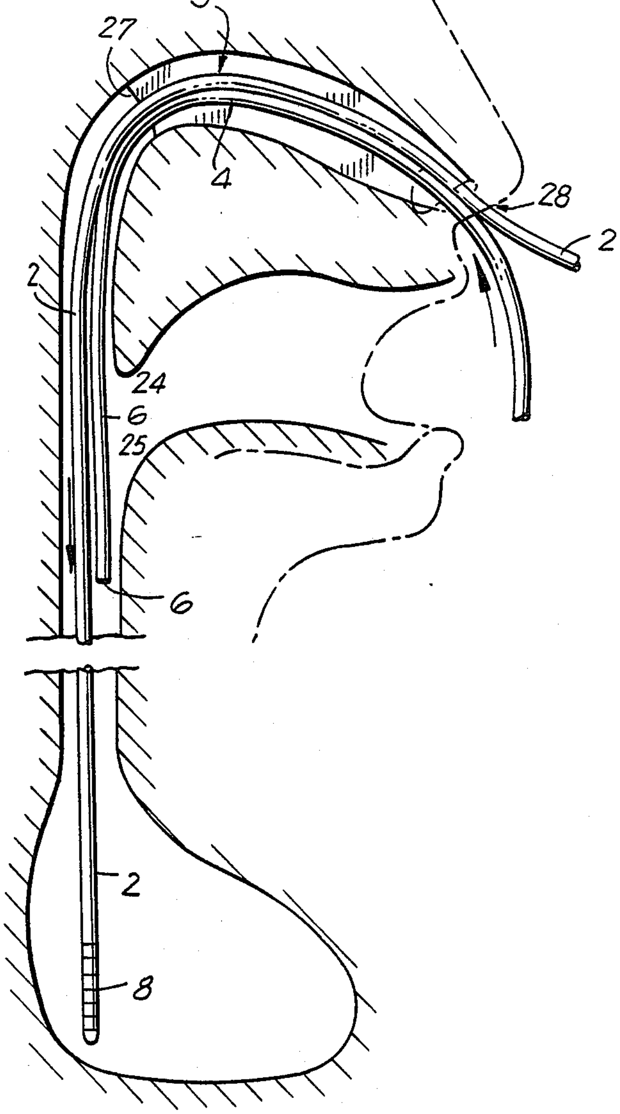
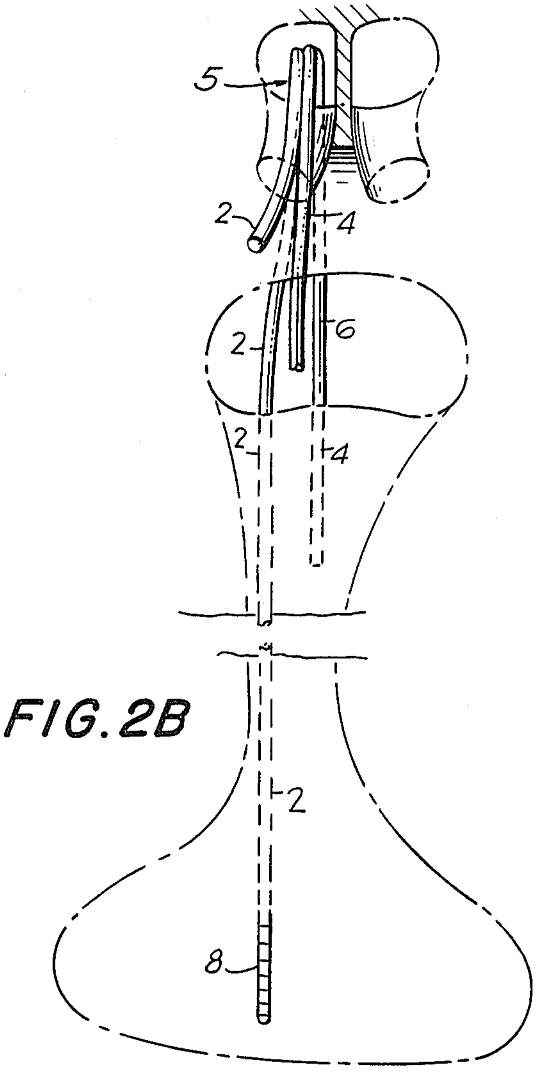
FIG. 2B

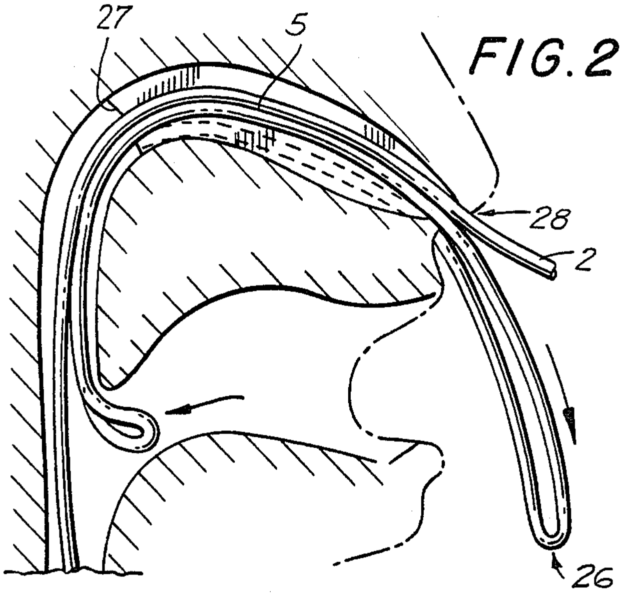
FIG. 2I
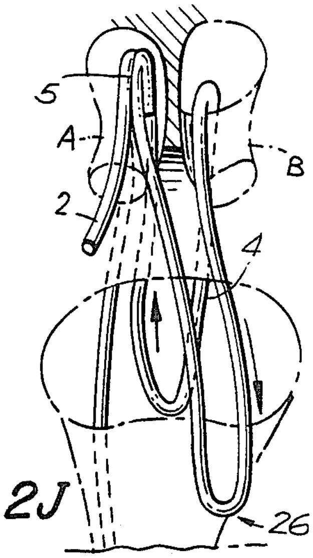
FIG. 2J
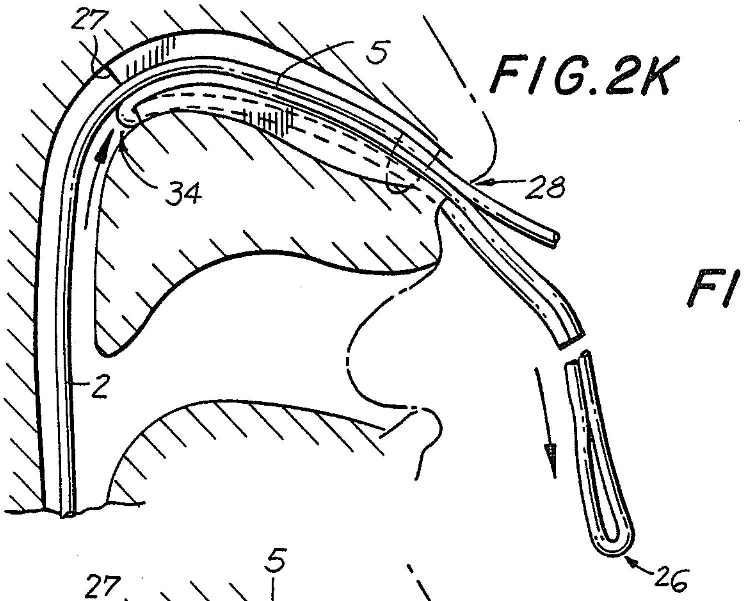
FIG. 2K
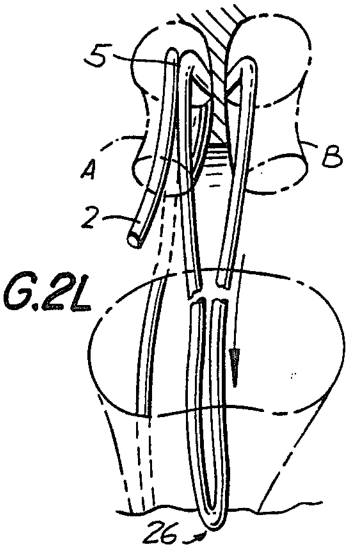
FIG. 2L
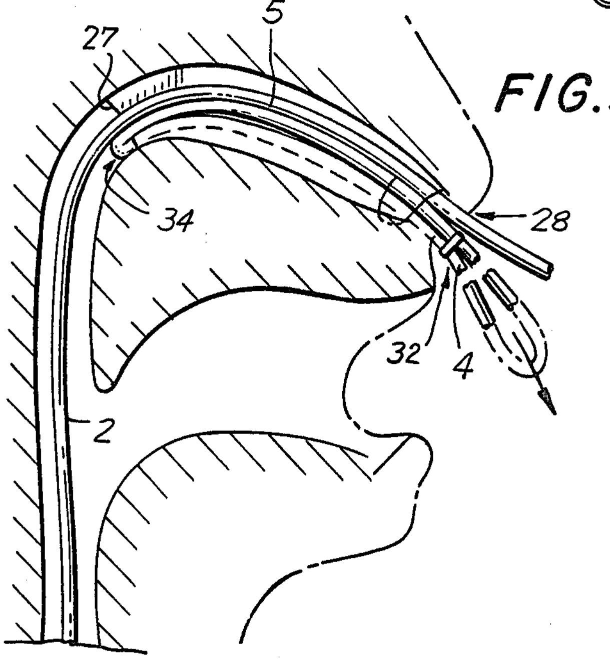
FIG. 2M
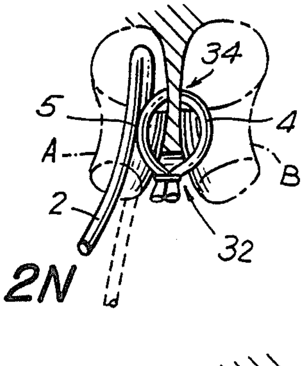
FIG. 2N
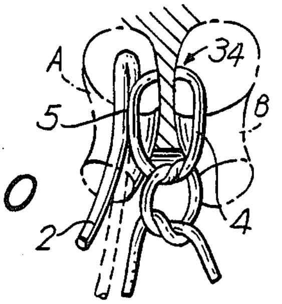
FIG. 2·O FIG. 3
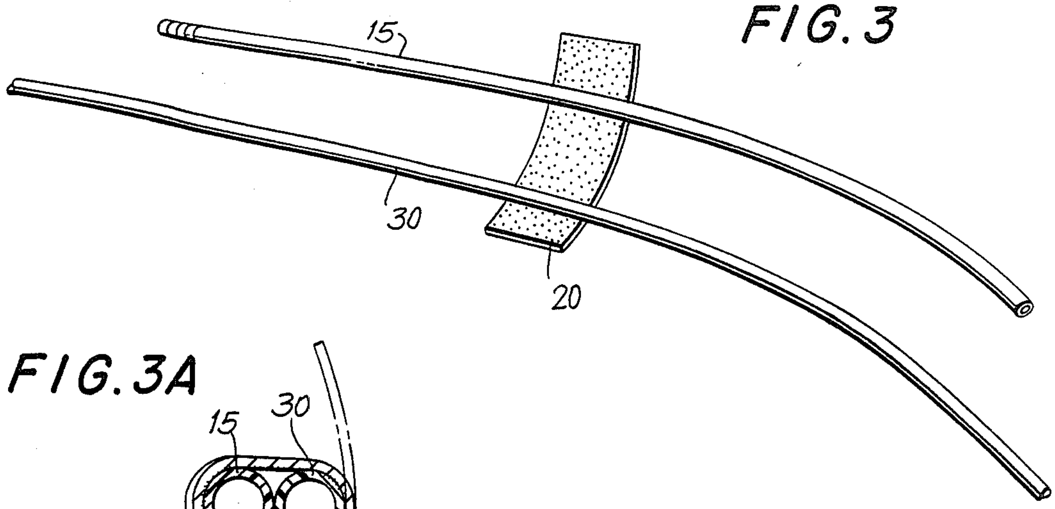
FIG. 3A
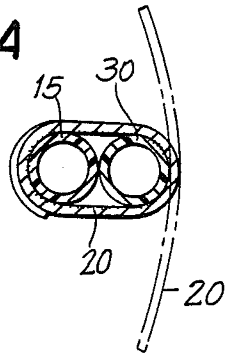
FIG. 4
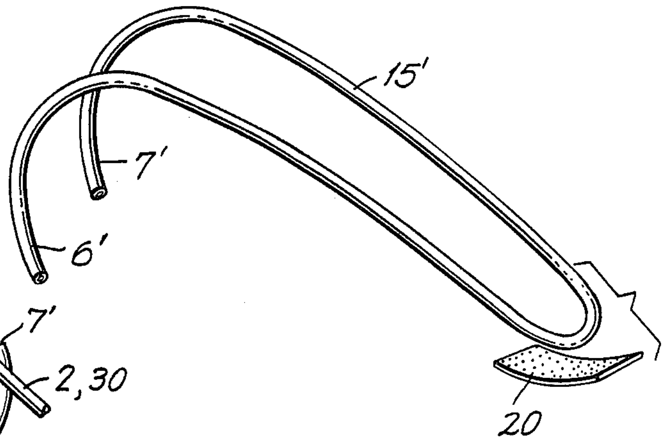
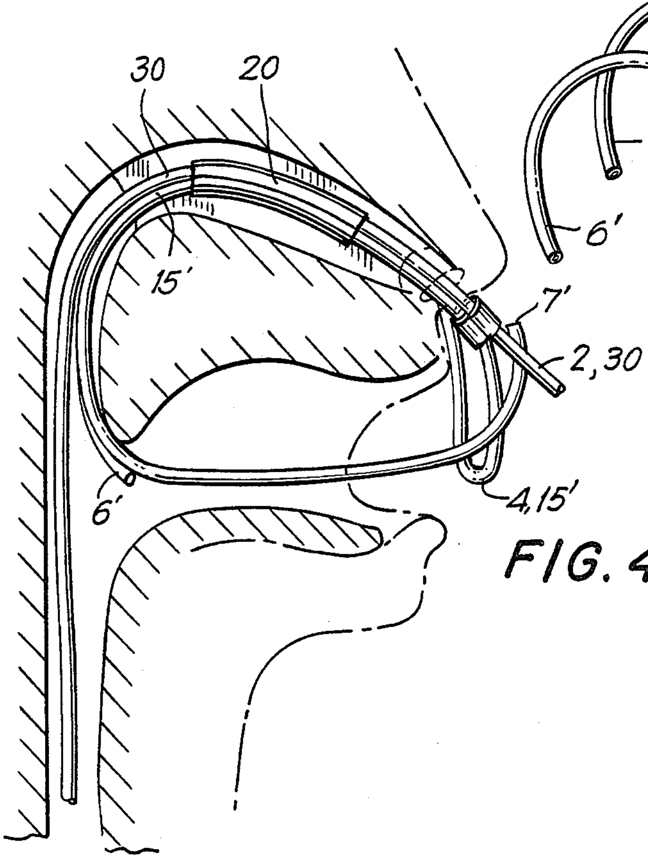
FIG. 4A

NASO-ENTERAL TUBE HARNESS APPARATUS AND METHOD

CROSS REFERENCE TO RELATED APPLICATION

This is a continuation-in-part application of application Ser. No. 774,485 entitled Naso-Enteral Tube Apparatus And Method, filed Sept. 10, 1985 in name of Jeffrey A. Meer, now issued as U.S. Pat. No. 4,634,425.

This invention relates to improvements in nasal tubes, and more particularly to a method and apparatus for securing nasal tubes to patients.

BACKGROUND OF THE INVENTION

Nasal tubes, also known as naso-enteral, naso-gastric, naso-duodenal, stomach tubes, or feeding tubes, collectively referred to as naso-enteral tubes, are used commonly in the course of patient health care, most frequently in preparation for, during, and after surgery. These tubes typically comprise a resilient plastic material such as polyurethane, polyethylene, or silicone, having a proximal end, a central lumen or passageway, a distal end, and optionally, a weight affixed to the distal end. The distal end may have one or more apertures providing for fluid flow in or out of the tube. In use, the tube is inserted upwardly into a patient's nostril, pushed along a path past the nasal pharynx, and then downwardly past the oral pharynx, through the esophagus and into the stomach, more preferably into the small intestine for feeding. A laterally flexible longitudinally rigid wire disposed within the central passageway may be used to aid insertion, the wire preferably being removed following proper placement of the distal end into the patient. Often, expensive and time-consuming extraordinary means may be required to aid proper tube placement in the patient. Such means may include, for example, x-ray fluoroscopy, direct placement with endoscopic visualization, or pharmacological assistance.

At the proximal end, a suction pump may be connected for using the tube for drainage of gastric secretions. Alternately, in connection with the preferred use, the tube may be connected to a supply of nutrient solution for naso-enteral feeding of the patient by passing liquid nutrient solutions through the tube directly into the stomach or small intestine. The latter use has become prevalent with improved techniques for developing and administering the nutrient solutions which are important for wound healing and tissue rebuilding, particularly in post operative head and neck cancer patients, patients having severe facial injury or reconstructive mouth surgery, and patients that are comatose or unwilling to eat, such patients otherwise having intact gastrointestinal tracts. Naso-enteral feeding is safer and less expensive than either intravenous or parenteral nutrition techniques, and typically occurs for intermediate periods lasting from a few days to several weeks or more.

A major problem with using in-dwelling naso-enteral tubes is that patients tend to pull them out prematurely, either deliberately, accidentally, or while disoriented. An unsecured or inadequately secured tube can also be displaced or removed by inattentive hospital staff, movement of the patient or tube-associated equipment, or by the patient coughing, sneezing, gagging or swallowing. Tube displacement, or extubation, is inconvenient for the physician and hospital staff and requires tube replacement for continued treatment, a time consuming and costly process, especially where extraordinary means are involved. Tube replacement also can be traumatic and discomforting to the patient, hazardous to a patient having fresh facial sutures, and it also may adversely affect the patient's emotional and physical well being. Further, extubation can be dangerous to the patient particularly if a tube is only partially removed which can result in the patient aspirating fluid into the lungs. In addition, time and resources must be spent in frequent monitoring of the patient, to make sure that the tube is properly in place and that either the nutrients are properly being administered to the stomach or suction is properly occurring.

Various techniques have been developed for securing a naso-enteral tube to the patient to prevent accidental or premature removal of the tube. Such techniques include using adhesive tape to secure the tube to the patient as shown in U.S. Pat. Nos. 4,114,626 and 3,046,989 and as illustrated in U.S. Pat. No. 4,282,871; using an adjustable or flexible tube holder for retaining the tube placed adjacent the nostril opening and secured to the patient by a harness going around the patient's head as shown in U.S. Pat. Nos. 2,831,487, 2,931,358, 3,161,199, 3,648,703, 3,972,321, 4,282,871, 4,284,076, and 4,480,639; a spectacle type frame secured to the patient by an elastic srrap about the head and having a means for securing the tube to the frame as shown in U.S. Pat. No. 3,209,775, a tube holder that has a self-attaching hook means that holds a nosepiece onto the nose as shown in U.S. Pat. No. 3,568,678; or an adhesive patch of Velcro TM on the patient's cheek and a corresponding patch secured to the tube. Among the problems associated with adhesive tape are that it stretches the skin, takes considerable time and effort to secure and release the tube, and loses effectiveness and must be replaced when the tape becomes wet. The problem with the aforementioned external harnesses is that they are clumsy, can be removed easily, for example, by an uncooperative patient, and can be easily dislodged accidentally, for example, during restless sleep. The harnesses that hold the tube frictionally generally use a means surrounding the tube which may be prone to sliding along the tube, or which compresses the tube, reducing the overall efficiency of fluid flow in the feed or drain system. Other problems with such harnesses include holding the tube in an unnaturally curved orientation relative to the nostril so that the tube bends or twists against the nostril or upper lip which may cause tissue erosion or increase the discomfort and aggravation to the patient. The harness also must be applied against the patient with enough pressure to keep the harness from moving and that pressure may cause localized pressure points on the tissue, minimizing the blood flow, and requiring frequent readjustment of the harness.

A further attempt to secure the tube to the patient has involved suturing the tube to the patient's tissue, for example the nasal columella. The problems with such stitching is that chronic pulling on the tube and constant nasal secretions may result in local infection and significant damage to the nasal columella, including, for example, sawing the columella in two.

Yet another technique involves passing one end of a web or tube through one nostril, down past the hypopharynx, retrieving both ends from the hypopharynx and securing the two ends together by suturing. The loop of web or tube at the base of the nasal columella is then pulled so that the tied ends of the tube pass back into the mouth, by the posterior aspect of the nasal septum, and out the nostril where the web or the tube is cut and tied together at the base of the columella. The knot may be sutured to prevent slippage. A naso-enteral tube is then inserted into the nostril and secured to the loop by sutures and adhesive tape. See Barrocas, A., Jastram, C., St. Romain, C., "The Bridle: Increasing the Use of Nasoenteric Feedings", *Nutritional Support Services,* Vol. 2, No. 8, August 1982. In an alternate form, the free ends of the loop are tied into a second knot about the naso-enteral tube where the naso-enteral tube may have a boss designed to prevent the tube from slipping relative to the loop. See McGuirt, W. F., Strout, J. J., "Securing of Intermediate Duration Feeding Tubes," *The Larvngoscope,* Vol. 90, pp. 2046–48 (1980).

The problem with these techniques is that they suffer the problems of all external harnesses in that the tube is secured to the harness at a location that the patient can reach and unsecure and remains subject to dislodgement or loosening by movement of the patient. The patient also may be able to remove the tube, for example, by reaching into their nostril behind the point of attaching the tube to the harness, grabbing the tube, and withdrawing it entirely or partially out of the nostril leaving the harness intact, and leaving the tube securely attached to the harness, leaving the harness securely fastened about the nasal septum.

In addition, the presence of sutures in or about the naso-enteral tube may weaken the structural integrity of the tube and may result in leakage of fluids outside the tube. If the sutures are too tight, they may restrict or cause a particle in the fluid to obstruct the lumen of the tube. This would interfere with the ability to pass fluids through the lumen and increase the the likelihood that the tube may be improperly used. Constant tugging on the tube may result in a sawing action, causing the tube to break. The knots or sutures may be broken by being pulled on or may become loosened by the constant nasal secretions or moisture, or may be untied or weakened by stress so that the naso-enteral tube can be slid or pulled out of the harness notwithstanding that the loop remains securely fastened to the patient. Further, these jury-rigged loops or bridles must be customized for each patient which is cumbersome and time-consuming for the doctor and may result in inconsistent results which could discourage use of an extremely beneficial feeding technique.

It is therefore an object of this invention to provide a simple and inexpensive apparatus and method for safe, consistent, anchoring of tubes to the patient's nasal septum that is comfortable, easy to secure, and substantially free of detrimental side effects such as tissue irritation and infection.

It is another object of this invention to provide a harness that will securely retain naso-enteral tubes without significantly occluding the tube lumen.

It is another object of this invention to provide an apparatus for securing a naso-gastic, naso-enteral, or other nasal tube to a patient that substantially will not slide relative to the harness while the harness is fixed in place.

It is yet another object of this invention to provide a harness for naso-enteral tubes that can be inserted and secured quickly with minimum discomfort to the patient, used for long periods of time, and is unobtrusive and not easily removed, intentionally or inadvertently, except by the application of proper cutting instruments.

SUMMARY OF THE INVENTION

The present invention comprises an apparatus and method for anchoring or securing tubes in a nostril of a patient, particularly naso-enteral tubes for use in nutrient solution feeding or gastic fluid drainage. The apparatus comprises a harness for securing a tube to a patient, a naso-enteral tube, and means for securing the harness to the naso-enteral tube along a length of the tube.

The naso-enteral tube comprises an elongated tubular member having a means for connecting the tube to a nutrient fluid supply or means for draining fluids from the patient at the proximal end, optionally a weight at the distal end for assisting in inserting and maintaining the distal end in the stomach or digestive tract, preferably in the duodenum or proximal jejunem of the small intestine, and typically has a plurality of perforations at the distal end for allowing the inflow or outflow of liquids depending upon the use of the tube.

The harness comprises an elongated body having a first end disposed toward the distal end of the tube and a second end disposed toward the proximal end of the tube. The first end is adapted to be passed through the nostril (nasal choana), preferably simultaneously with insertion of the naso-enternal tube in a first nostril. The second end of the harness is adapted to be inserted into the second nostril and connected to the first end so that the first and second ends may be secured together to form a loop passing through both nostrils that can be adjusted to fit closely about the nasal columella and the posterior aspect of the nasal septum. In the preferred embodiment, the harness comprises a material similar to or compatable with the naso-enteral tube, for example, polyurethane, polyethylene, or silicone.

The means for securing the harness to the naso-enteral tube may comprise any conventional means including but not limited to (1) an adhesive, (2) a web of material resulting from coextrusion of the tube and harness, (3) thermal, dielectric, or ultrasonic welding, or (4) application of a material web or tape, resistant to body fluids, joining the naso-enteral tube and harness together for a distance along the length of the tube. The means must be compatible to secure the tube to the harness. The distance is preferably less than the distance between the posterior aspect of the nasal septum and the base of the nasal columella of the patient for a preselected range of sizes. More preferably, the length of the distance is less than half the distance between the posterior aspect of the nasal septum and the base of the nasal columella so as to provide a device adaptable to a wider range of patients of different sizes. In one embodiment, the harness may be wrapped or coiled about the tube so as to increase the holding power of the harness.

The preferred method of this invention comprises inserting the first end of the harness and the distal end of the naso-enteral tube into one of the nostrils ("first nostril") of the patient so that the distal end of the tube is located at the desired location in the patient, a portion of the harness is visible in the hypopharynx and the distance along the length of tubing to which the harness is secured is substantially within the nostril between the base of the nasal columella and the posterior aspect of the nasal septum. The portion of the harness visible in the hypopharynx is then extracted and pulled out the mouth. The second end of the harness is then passed through the other nostril ("second nostril") until it is visible in the hypopharynx and it is then pulled out of the mouth. Preferably, Magill forceps or an equivalent are used to extract the harness. The first and second ends of the harness are then secured together. In accordance with prior practices, the ends may be secured together, side by side, by sutures, tape, or both, or tied into a small knot such as a square knot, with or without sutures. These steps are time-consuming, difficult in an uncooperative patient and can result in a connection that may be difficult to pull through the nasal cavity. In the preferred embodiment, the ends of the harness may be interlocking or interfitting. For example, the end passing into the first nostril may have a male protrusion and the end passing into the second nostril may have a female receptacle for receiving the male protrusion for frictionally interconnecting the ends together. Alternately, a separate piece, insertable into or about both ends of the harness, may be used to secure the harness ends together into a loop. The advantages of the interfitting ends are that it significantly reduces the time needed to connect the ends of the harness together outside the mouth as no suturing is required, and the end to end connection facilitates smooth passage of the harness through the nasal cavity without catching on the patient's sinus or nasal cavities. Reducing the time factor is important because the more stress there is on the patient's soft palate during interconnection of the harness, the more likely the patient will vomit or attempt to pull out the tube and harness during the insertion process.

In an alternative embodiment, the harness may comprise a webbing of material secured to the tube, the ends of which may be tied together and optionally stitched.

The portion of the harness extending out the second nostril is then pulled so that the first and second ends, secured together, pass back into the mouth, up the hypopharynx and out the second nostril and the portion of the harness inside the nasal cavity is resting against the posterior aspect of the nasal septum. The portion of the harness extending out of the first and second nostrils is then cut and the harness is secured together, for example, by tying a square knot and suturing the knot together, or by suturing the ends together so that the harness closely surrounds the nasal septum and nasal columella, thereby securely fastening the naso-enteral tube within the patient's nasal cavity. However, the fit must not be so tight as to cause tissue erosion or pressure necrosis, nor so loose as to permit a patient to place a finger inside the loop without considerable effort. Further, the close fit would minimize the likelihood that a patient could reach into their nostril, grab the tube behind the point at which the tube is secured to the harness, and withdraw the tube. For example, a tube secured to a harness for a distance extending at least a half inch into the nostril from the nostril opening, would minimize the likelihood of such an extraction by most patients. The patient pulling on the tube or on the loop is thereby discouraged from continuing to withdraw the tube by the pressure exerted by the harness on the posterior aspect of the nasal septum. The naso-enteral tube may be removed when the harness is intentionally severed, for example, at the termination of scheduled treatment, and can be drawn easily out through the first nostril.

In an alternate embodiment, the ends of the harness may be inserted and secured together before the naso-enteral tube is inserted. Then the naso-enteral tube is inserted so that the distance along the length where the harness is joined to the tube is located in the nasal cavity. Finally, the harness is secured closely about the nasal septum.

It may be advantageous to make the harness a different color than the feeding tube, particularly for distinquishing the tube and harness when extracting the ends of the harness. It also may be advantageous to tack the end of the harness inserted in the nostril with the feeding tube to promote easy simultaneous insertion of the tube and harness as long as the tacking means, e.g., an adhesive, is either an edible, digestable, or non-toxic material which permits separation of the harness from the tube without disturbing the location of the distal end of the tube. It also may be advantageous with soft harness tubes to provide the ends of the harness with flexible, gently curved end sections or to use an insertion wire having a gently curved end section to insert the harness so that during insertion the curved harness ends will follow the typical anatomical curve along the bottom of the nostril, and, upon passage through the nasal pharynx, pass directly into the mouth. This would substantially minimize having to use the time consuming step of withdrawing the harness end out of the hypopharynx with Magill forceps and further, reduce annoyance and discomfort to the patient, and the time required to insert a harness.

During insertion, it may be advantageous to lubricate, anesthetize, or do both to the patient, at least topically, to decrease gagging. The length of the naso-enteral tube and the location and length of the distance along the tube that the harness and tube are secured together may be selected in a size appropriate for the size of the patient. For feeding patients, one size tube may be adapted for use in a large range of differently sized patients because the area in the small intestine that is optimal for the infusion of nutrient solutions extends at least from the duodenum to the proximal jejunem, which is a substantial distance of about a foot. This permits an added economy in permitting use of one tube length for many patients of a given size range, thereby reducing the need to customize tubes and harnesses for each patient. The length of tubing having the harness secured thereto at a preselected location also may be adjusted by cutting the distal end to an appropriate length and, optionally, affixing a weight to the end.

In an alternate embodiment, the harness is formed as a separate item comprising the first and second ends and a securing means and is adapted to be secured to a tube just prior to insertion. Preferably, the securing means is an adhesive coated material or web attached to the harness at the location along the harness corresponding to the distance along the length of tube that will be inside the patient's nostril. The web may be provided with, for example, a tacky adhesive and a conventional coated paper release strip so that the release strip may be removed from the adhesive coating and the web then applied to secure the harness to the tube to be inserted. A variety of adhesives or securing means could be used including, but not limited to, a polyurethane strip or flap coated on one side with a vinyl acrylate or vinyl acetate type adhesive, for example, the commercial product known as Ensure-it TM, Catalog No. 38-1200-1, manufactured by Deseret Medical, Inc., Sandy, Utah. In yet another embodiment, the harness and the web having an adhesive material also may be separate items so that the web may be wrapped around both the harness and the tube to secure them together for a distance along their length, e.g., from about an inch to about an inch and a half, prior to insertion.

In an alternate embodiment, the strength of the connection between the harness and the naso-enteral tube may be controlled so that a patient, intentionally attempting to pull the tube out, will cause the tube to separate from the harness rather than break within the nasal septum, which may cause fluids present to be aspirated into the lungs. The strength of the joint also can be controlled so that the tube and harness will separate before the posterior aspect of the nasal septum is damaged. In yet another embodiment, the harness could have a tensile strength less than the feeding tube or be designed to break at a preselected location, for example, near the posterior aspect of the nasal septum, so that the harness will break rather than have the tube separate from the harness when the tube is pulled persistently, to reduce the risk of injury to the patient, especially the nasal septum.

BRIEF DESCRIPTION OF THE DRAWING

FIG. 1 is a perspective view of a naso-enteral tube in accordance with the present invention.

Figure 2C:
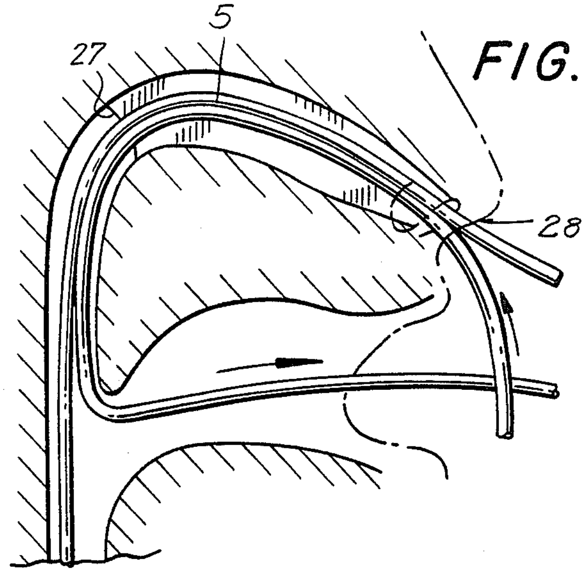

FIGS. *2a–2o* are a series of schematic views of the naso-enteral tube of FIG. 1 being inserted into and secured within a patient in accordance with the present invention. FIGS. *2a, 2c, 2e, 2g, 2i, 2k,* and *2m* are side sectional views of a patient taken along a line through nostril A. FIGS. *2b, 2d, 2f, 2h, 2j, 2l, 2n,* and *2o* are front sectional perspective views.

FIG. 3 is a perspective view of a harness in accordance with the present invention.

FIG. *3a* is a cross sectional representation of a harness and tube before and after application of an adhesive web in accordance with the present invention.

FIG. 4 is an elevated perspective view of a harness in accordance with the present invention.

FIG. *4a* is a cross sectional view of the harness of FIG. 4 in a patient in accordance with the present invention.

DETAILED DESCRIPTION OF THE INVENTION

An improved naso-enteral tube is shown in FIG. 1. A feeding solution supply (not shown) may be connected to connector 1 of naso-enteral tube 2 for passing the feeding solution directly to the patient's stomach or small intestine. Alternately, a suction pump can be attached to connector 1 for draining gastric fluids. Tube 2 may be any sized conventional naso-enteral tube and is preferably a polyurethane Dobhoff-type feeding tube, about 36 to 43 inches long, such as an Extriflex™ feeding tube Model No. 8 French, 43 inches long, made of a Erythrothane® polyurethane, commercially available from Biosearch Medical Products Inc., Raritan, N.J. Weight 8 is affixed to the distal end of tube 2 inserted into the patient, for promoting intubation of the small intestine and tube passage through the pylorus, and for aid in anchoring the tube against movement. Secured to tube 2 for a distance along the length of tube 2 at location 5 is harness 4, comprising a length of flexible resilient material, preferably an elongated cylindrical structure having a different color than tube 2. Harness 4 may be made of polyethylene or polyurethane, for example, and may be about eighteen inches long. Any means of permanent securement may be used at location 5 including but not limited to (1) coextrusion of tube 2 and harness 4, (2) joining tube 2 and harness 4 with adhesives, (3) wrapping with a tape, (4) thermal welding, (5) ultrasonic welding, (6) dielectric welding, or the like. In the preferred embodiment, harness 4 is adhered to tube 2 by an adhesive such as methyl ethyl ketone, tetra hydro furan (THF), or an equivalent, which can provide a stronger or weaker bond as appropriate for the patient.

Referring to FIGS. 3 and *3a*, an alternate embodiment is shown. Securing means 20 may be first secured to the harness by any of the aforementioned techniques or may be formed as an integral part of the harness. In the most preferred embodiment, securing means 20 is a flexible web or sheet of material, solid or fabric, coated with an adhesive capable of adhering securely to tube 30, but not significantly degraded in effectiveness by nasal secretions and moisture commonly present in a nostril. A release paper (not shown) covering the adhesive may be provided to prevent degradation of adhesive quality during storage and prior to application to a tube. For example, the release paper may be removed just prior to use and securing means 20 applied about tube 30 for the distance along the length, e.g., 1–1.5 inches for average adult patients, so that when tube 30 and harness 15 are inserted in place and harness 15 secured about the nasal septum, securing means 20 is within the patient's nostril. FIG. *3a* shows the adhesive sheet, tube and harness before secured together in phantom, and after secured together in solid lines.

Preferably, the adhesive coated web may include a polyurethane sheet or web coated on one side with a vinyl acrylate adhesive. Such a coated material, known as Op-site™ manufactured by Smith and Nephew, has been applied to a typical naso-enteral tube and submerged under water for a period of about three days. No weakening of the adhesive connection was discovered, indicating that such adhesive coated webs are sufficient for securing the tube to a harness within the moist environment of a patient's nostril.

Other types of securing means may be used other than tacky adhesives. In the most preferred embodiment, the web of material preferably extends all this way around tube 30 and may overlap itself. The strength of the retention force of the web may be adjusted for example, by adjusting the size of the web, the tear strength of the web (e.g., providing a series of perforations designed to separate under a given force), the quantity and peel off strength of the adhesive, the surface area of adhesive in contact with tube 30, and the amount of overlap of web 20 on itself when applied to tube 30, harness 15, or both.

Desirably, harness 4 (or harness 15 or 15') has a weaker tensile strength than tube 2 (or tube 30) so that if the patient is insistent upon pulling out tube 2, harness 4 will break before the feeding tube breaks or separates from the harness and before there is damage to the nasal septum. This would permit removal of tube 2 intact along with harness 4. Alternately, the tensile strength could be weaker at preselected location 34 about the posterior aspect of the nasal septum, shown in FIG. *2m*, or the harness could be provided with a tearable score permitting the harness to separate under a preselected force. In some circumstances it may be desireable to have tube 2 separate from harness 4 at location 5 before the harness breaks, leaving the harness secured about the nasal septum. In other circumstances, for example, where the danger of aspirating fluid into the lungs is particularly high, it may be desirable to have tube 2 break leaving a portion of tube 2 properly seated and still secured to harness 4 and harness 4 intact about the nasal septum, to substantially reduce the likelihood of fluid entering the lungs. These situations can be achieved by selecting materials with appropriate tensile strengths and adjusting the strength of the means securing tube 2 to harness 4 accordingly.

In operation, the patient, particularly the patient's nostrils and pharynx, may be first anesthetized with a topical anesthetic which will ease insertion of the tube by reducing gagging of the pharynx and rejection of the tube by the patient, and also may act to lubricate the nasal passages, facilitating insertion.

Figure 2D:
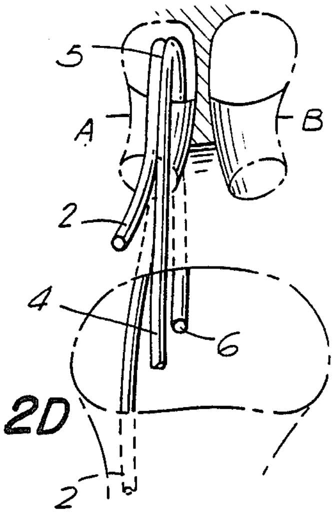
Figure 2E:
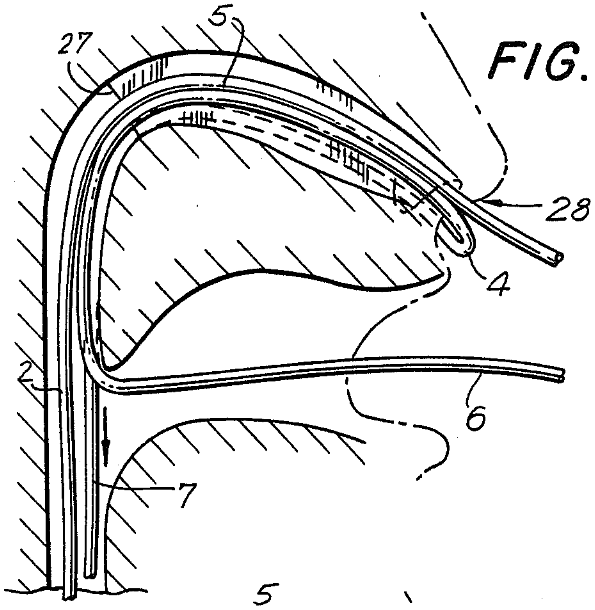
Figure 2F:
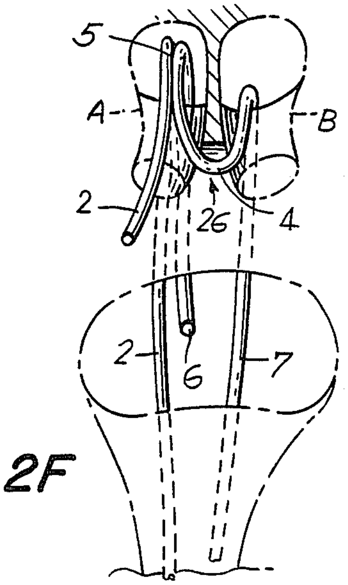
Figure 2G:
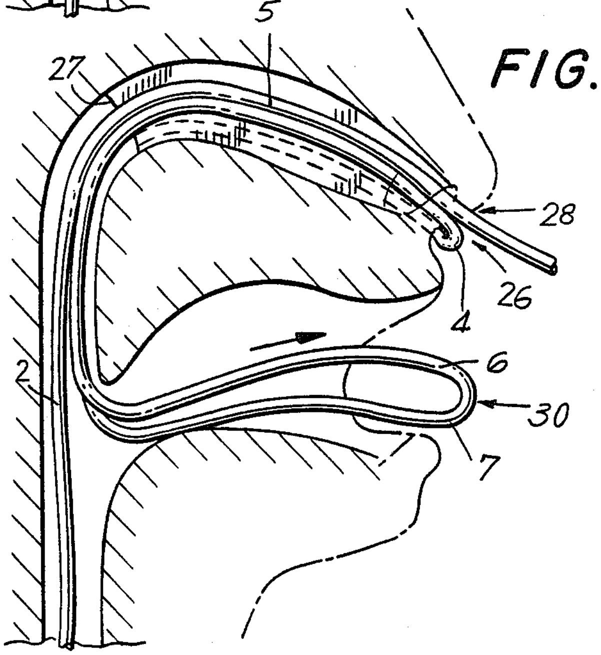
Figure 2H:
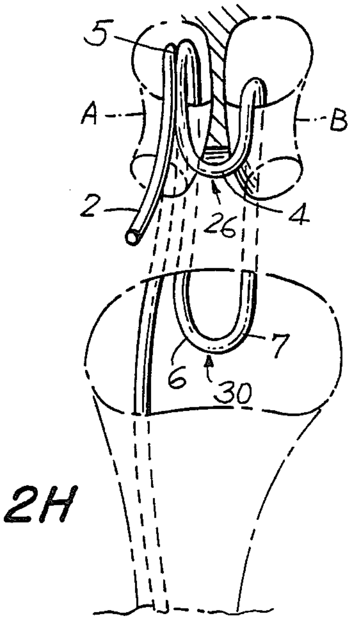

Referring to FIGS. 2*a*–2*d* the improved naso-enteral tube 2 and harness 4 are simultaneously inserted in one of the patient's nostrils (nostril A) until location 5 is within the nasal cavity between the base of the nasal columella 28 and posterior aspect of the nasal septum 27, the distal end of tube 2 is properly located in the patient, harness portion 6 passes hypopharynx 24 or pharynx 25, and the harness can be extracted and pulled out of the mouth by a tool such as Magill forceps or the like. Referring to FIGS. 2*e*–2*h*, portion 7 of harness 4 is then passed inwardly through the other nostril (nostril B) and similarly pulled out the mouth. The ends of portions 6 and 7 are then connected together outside the mouth (FIGS. 2*g*, 2*h*), for example, by inserting a protusion on end portion 6 into a complementary receptacle on end portion 7 to form a substantially continuous harness tube at location 30. In alternate embodiment, the connection may be by suturing or tying together in a small knot (not shown) that may be passed through nostril B, without damaging the patient.

Referring to FIGS. 2*i*–2*o*, harness 4 is then pulled at location 26 so that the interconnected ends of harness 4 re-enter the mouth and then pass out through nostril B (FIG. 2*l*). Harness 4 is pulled close against the back of nasal septum 27 within the patient's skull. Ends 6 and 7 may then be separated and reconnected together at the base of nasal columella 28 by knotting (FIG. 2*o*) or tied with suture 32 (FIG. 2*n*), for example, a silk suture in the range of 2.0 to 3.0, preferably 3.0 silk, so that the patient cannot easily place an object such as a finger between the harness and the base of nasal columella 28. If a knot is used, it also may in turn be sutured together securely, to reduce the likelihood that the ends will be untied, loosened, or otherwise separated. The excess harness material may be then cut off. Thus, feed tube 2 is securely harnessed about the patient's nasal septum 27 and columella 28 substantially preventing inadvertent removal and inhibiting unauthorized intentional withdrawal.

In an alternate embodiment, the method could comprise first forming the harness loop substantially as described above, inserting tube 2 into nostril A until the distal end is properly located in the patient and location 5 is within the patient's nasal cavity, and then adjusting the fitting of the harness loop to fit closely about the patient's nasal columella and nasal septum.

Referring to FIGS. 4 and 4*a*, harness 15' having gently curved ends are shown. Although the amount of curve may vary depending upon the size of the patient, for an adult male typical dimensions would involve placing a curve along the end two inches of harness ends 6' and 7' having a radius of about two inches. The curve must not be so radical to get caught in the sinus or other nasal passages during insertion, but must be substantial to advance into the mouth for easy extraction. The curve may be impressed upon the harness during manufacture or prior to insertion, for example, by an appropriately curved flexible insertion wire. Such a harness must be sufficiently soft and flexible so that a curved end will deflect from and move along rather than damage the nasal tissues. A soft harness will also permit rotating the harness after it is inserted to correct the harness curve orientation so that the curve properly urges end 6' or 7' into the mouth rather than the hypopharynx without damaging the patient. The harness can then be fastened together as described herein.

Other means for reducing irritation to the patient caused by inserting the harness may be employed. For example, if the harness is a solid rod or hollow tube, the ends may be provided with a radius to promote insertion, removing sharp corners. The harness may be a substantially hollow tube except for the very end portion, the end being a solid rod. Insertion may in this instance be aided by a longitudinally rigid and laterally flexible guide wire passing inside the tube core, preferably having the aforementioned gently curved end configuration. After withdrawing the tube out the mouth (and withdrawing the guide wire), the solid end piece can be cut off leaving a female receptacle adapted for receiving an appropriately sized male protrusion. Alternately, both ends of the harness could be provided with tapered solid end pieces to facilitate insertion, the degree of taper being designed so that one of the tapered ends will fit into the core of the tube of the other end of the harness when the solid portion of that end has been cut off. The harness ends may then be interconnected, pulled into the mouth and out the nostril, and secured together about the nasal septum. In another embodiment, a separate piece could be inserted into the hollow core of both ends to interconnect the ends together to form a loop. Alternately, if the harness is a solid rod, the ends could be tapered to fit into a separate section of hollow tube adapted for interconnecting the harness ends together for withdrawal out the nostril.

Removal of the feeding tube secured by a harness in accordance with this invention may be accomplished by severing the harness and extracting the tube and harness out nostril A.

This invention is equally applicable to secure any tube passing into the patient's nostril. As various changes can be made in the above constructions without departing from the scope of the invention, it is intended that all matter contained in the above description or shown in the accompanying drawings shall be interpreted as illustrative and not in a limiting sense.

I claim:

1. Apparatus for use in securing a tube in a nostril about the nasal septum of a patient comprising a harness having a first end, a second end, and a securing means, the first end for passing through the same nostril as the tube, the second end for passing through the other nostril, the first and second ends being adapted for fastening to each other about the nasal septum, and the securing means being adapted for securing the harness to the tube for a distance along the length of the tube before the tube is inserted completely into the nostril so that there will be substantially no relative movement between the harness and the tube along said distance, wherein the securing means further comprises a web of material secured to the harness between the first and second ends having an adhesive coating and adapted for contacting the tube so that the adhesive coating will secure the harness and tube together before the tube is inserted completely into the nostril and said distance of the harness and tube secured together being adapted to be passed into the same nostril as the tube.

2. The apparatus of claim 1 further comprising release means for permitting the tube to be pulled out of the nostril by a force greater than a predetermined force.

3. The apparatus of claim 2 wherein the release means further comprises a section of harness having a tensile strength substantially equal to the predetermined force so that a force pulling on the tube greater than the harness tensile strength will cause the harness to break.

4. The apparatus of claim 2 wherein the release means further comprises the securing means having a maximum retention force substantially equal to the predetermined force so that a force pulling on the tube greater than the maximum retention force will cause the tube to separate from the harness.

5. The apparatus of claim 1 further comprising means for tacking the first end to the tube prior to insertion of the tube.

6. Apparatus for use in securing a tube in a nostril about the nasal septum of a patient comprising a harness having a first end, a second end, and a securing means, the first end for passing through the same nostril as the tube, the second end for passing through the other nostril, the first and second ends being adapted for fastening to each other about the nasal septum, and the securing means being adapted for securing the harness to the tube for a distance along the length of the tube before the tube is inserted completely into the nostril so that there will be substantially no relative movement between the harness and the tube along said distance, wherein the first and second ends each further comprise a curvature having a preselected radius, the radius being selected for urging the first and second ends, into the patient's mouth after passing the nasal pharynx.

7. The apparatus of claim 6 wherein the radius further comprises about a two inch radius of curvature extending for about two inches from the end of the first and second ends, the rest of the harness having substantially no preselected curvature.

8. A method for securing a tube to a patient comprising:

attaching a harness to the tube for a distance along the length of the tube, the harness having a first and second end;

inserting the tube at least partially into a first nostril and inserting the first end of the harness into the first nostril so that the first end passes through the first nostril past the nasal pharynx;

inserting the second end of the harness tube into the second nostril past the nasal pharynx;

securing the first and second ends of the harness together;

pulling the harness out of the second nostril so that the first and second ends of the harness pass out the second nostril and said distance where the harness and the tube are secured together is substantially within the first nostril; and severing the harness outside the nostrils and securing the harness together closely about the nasal septum and nasal columella.

9. The method of claim 8 wherein securing the harness closely about the nasal septum and nasal columella further comprises securing the harness so that said distance is substantially within the first nostril and substantially beyond the reach of a patient attempting to reach the tube behind said distance.

10. The method of claim 8 wherein inserting the harness ends further comprises passing the ends of the harness directly into the patient's mouth after passing the nasal pharynx, said harness ends having a predetermined curvature adapted to facilitate such passage.

11. The method of claim 8 wherein inserting the harness ends further comprises passing the ends of the harness into the hypopharynx after passing the nasal pharynx.

12. The method of claim 8 wherein securing the first and second harness ends together further comprises interconnecting the harness ends together by inserting one of the harness ends having a male fitting into a female receptacle on the other end to frictionally connect the ends together.

13. The method of claim 8 wherein securing the first and second ends together further comprises interconnecting one end of the harness into one end of a separate piece of material and interconnecting the other end of the harness to the other end of the separate piece of material to form a loop that can be passed through the patient's nostril without separating or catching on the nasal passageway.

* * * * *